United States Patent [19]

Scherer, III

[11] Patent Number: 4,952,868
[45] Date of Patent: Aug. 28, 1990

[54] MOISTURE SENSING SYSTEM FOR AN IRRIGATION SYSTEM

[76] Inventor: Robert P. Scherer, III, 619 N. Cataract Ave., San Dimas, Calif. 91773

[21] Appl. No.: 258,775

[22] Filed: Oct. 17, 1988

Related U.S. Application Data

[63] Continuation-in-part of Ser. No. 864,421, May 19, 1986, Pat. No. 4,837,499.

[51] Int. Cl.$^5$ ................. G01R 27/00; F16K 13/02
[52] U.S. Cl. ....................... 324/664; 239/63; 137/78.3; 324/690
[58] Field of Search ............... 324/65 P, 65 R, 61 P, 324/443, 446, 448, 450, 96; 73/73, 75; 239/63; 137/78.3

[56] References Cited

U.S. PATENT DOCUMENTS

| | | | |
|---|---|---|---|
| 2,578,981 | 12/1951 | Parker | 299/27 |
| 2,599,862 | 6/1952 | Ray | 299/25 |
| 2,695,976 | 11/1954 | Hasenkamp | 315/76 |
| 2,737,615 | 3/1956 | Roby, Jr. et al. | 317/141 |
| 2,766,028 | 10/1956 | Robinson | 299/27 |
| 2,768,027 | 10/1956 | Nelson | 299/1 |
| 2,785,006 | 3/1957 | Young et al. | 299/25 |
| 2,796,291 | 6/1957 | Mueller | 299/25 |
| 2,812,976 | 11/1957 | Hasenkamp | 299/27 |
| 2,941,174 | 6/1960 | Richards | 324/65 P |
| 2,985,827 | 5/1961 | Hasenkamp | 324/446 X |
| 3,039,698 | 6/1962 | Richards | 239/64 |
| 3,079,089 | 2/1963 | Tomayer | 239/63 |
| 3,114,243 | 12/1963 | Winters | 61/12 |
| 3,182,914 | 5/1965 | Hosier | 239/63 |
| 3,206,615 | 9/1965 | LaPointe | 307/88.5 |
| 3,224,676 | 12/1965 | Rauchwerger | 239/63 |
| 3,238,392 | 3/1966 | Richards | 307/116 |
| 3,356,979 | 12/1967 | Bouyoucos | 338/35 |
| 3,437,924 | 4/1969 | Tocanne | 324/61 |
| 3,488,000 | 1/1970 | Cramer | 239/63 |
| 3,500,844 | 3/1970 | Sanner | 137/78 |
| 3,520,476 | 7/1970 | Schmid | 239/63 |
| 3,553,481 | 1/1971 | Hasenbeck | 239/63 |
| 3,599,867 | 8/1971 | Griswold et al. | 239/63 |
| 3,626,286 | 12/1971 | Rauchwerger | 324/61 |
| 3,642,204 | 2/1972 | McCloskey | 239/63 |
| 3,782,179 | 1/1974 | Richards | 73/73 |
| 3,847,351 | 11/1974 | Hasenbeck | 73/75 X |
| 3,867,837 | 2/1975 | Malin | 73/73 |
| 3,882,383 | 5/1975 | Matlin | 324/65 R |
| 3,991,939 | 11/1976 | Maclay | 239/63 |
| 4,137,931 | 2/1979 | Hansenbeck | 137/78 |
| 4,190,884 | 2/1980 | Medina | 364/104 |
| 4,194,691 | 3/1980 | Birnbach et al. | 239/63 |
| 4,197,866 | 4/1980 | Neal | 137/1 |
| 4,216,789 | 8/1980 | Hasenbeck | 137/78 D |
| 4,246,574 | 1/1981 | Sanner | 340/602 |
| 4,253,606 | 3/1981 | Johnson | 239/63 |
| 4,256,133 | 3/1981 | Coward et al. | 137/78.3 |
| 4,290,146 | 9/1981 | Adolfsson et al. | 324/96 X |
| 4,333,490 | 6/1982 | Enter, Sr. | 137/78.3 |
| 4,396,149 | 8/1983 | Hirsch | 239/63 |
| 4,531,087 | 7/1985 | Larson | 324/65 P |
| 4,540,936 | 9/1985 | Walsh | 324/61 P |
| 4,734,554 | 3/1988 | Tateda et al. | 73/73 X |

FOREIGN PATENT DOCUMENTS

| | | | |
|---|---|---|---|
| 259300 | 6/1965 | Australia | 324/61 P |
| 2062246 | 5/1981 | United Kingdom | 324/61 P |

*Primary Examiner*—Reinhard J. Eisenzopf
*Assistant Examiner*—Jack B. Harvey
*Attorney, Agent, or Firm*—Harness, Dickey & Pierce

[57] ABSTRACT

A moisture sensing device for an irrigation system. A pair of concentrically disposed cylindrical conductors are separated by a layer of beads, such that a capacitor is formed whose resistance will vary in response to the level of moisture present in the fibrous material. An electrical circuit is connected across the cylindrical conductors for measuring the variable resistance caused by the level of moisture present in the layer of beads. If the soil is dry enough to require watering, the sensor circuit will produce an output signal to the appropriate solenoid in the irrigation system to permit watering.

13 Claims, 6 Drawing Sheets

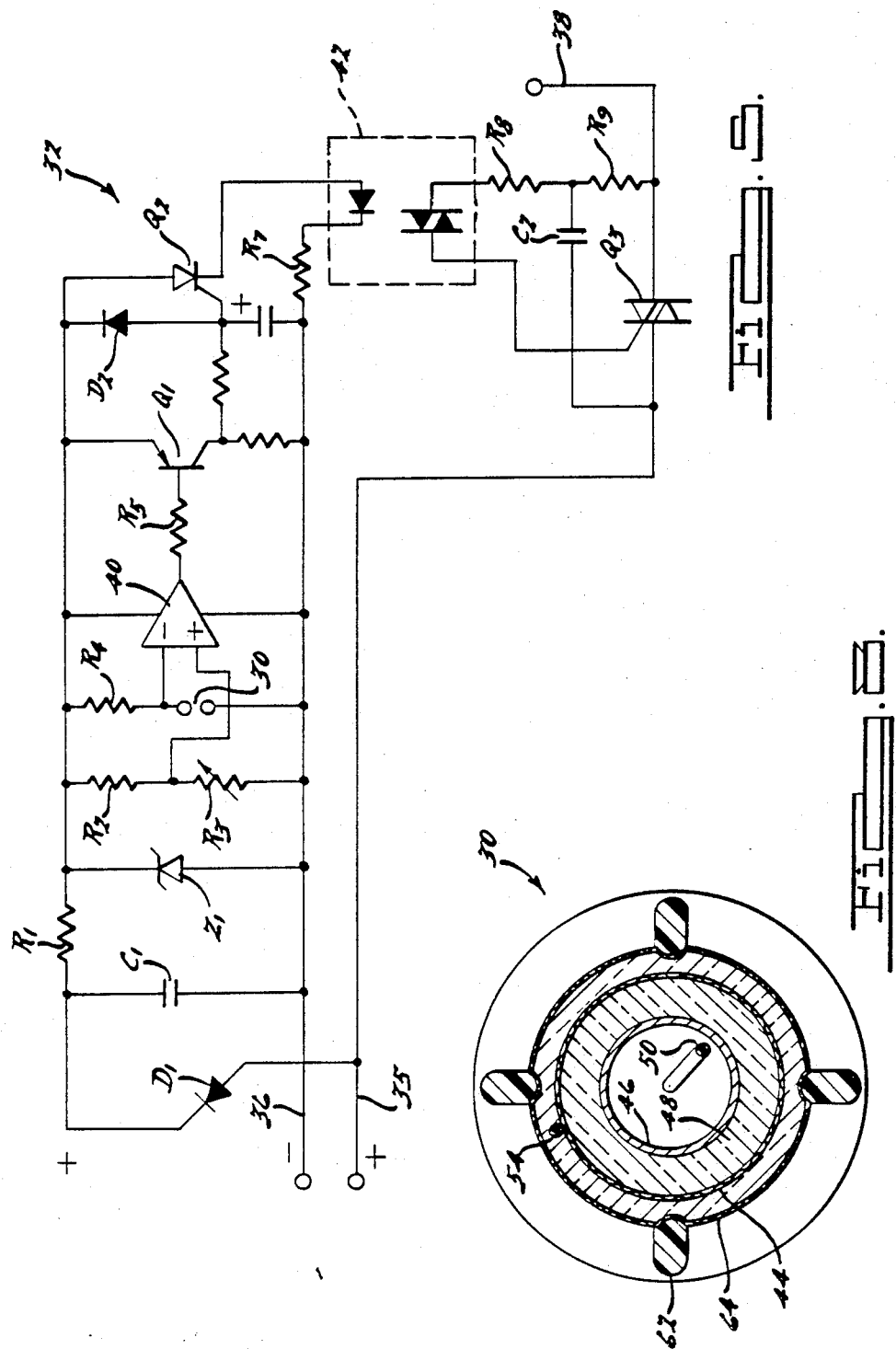

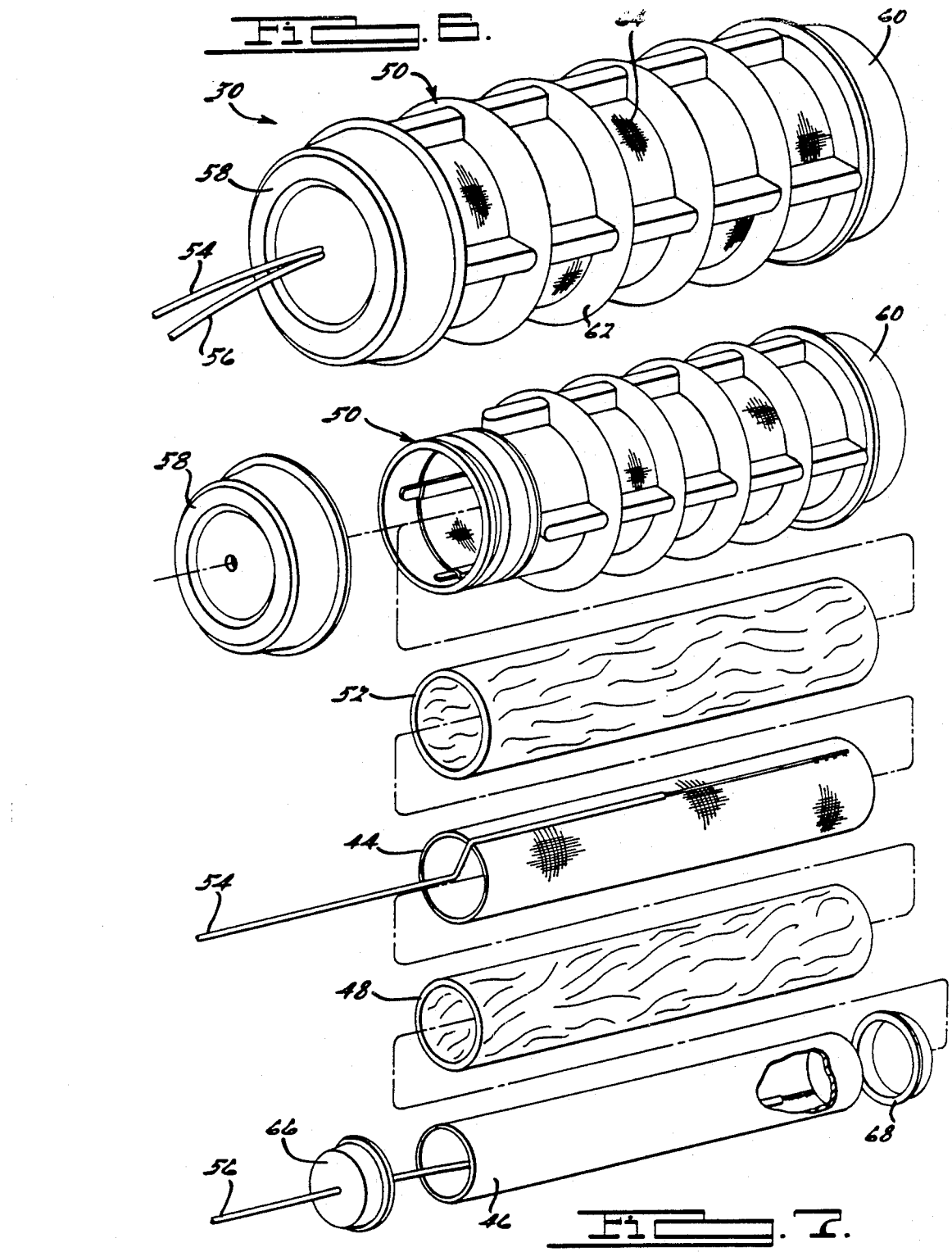

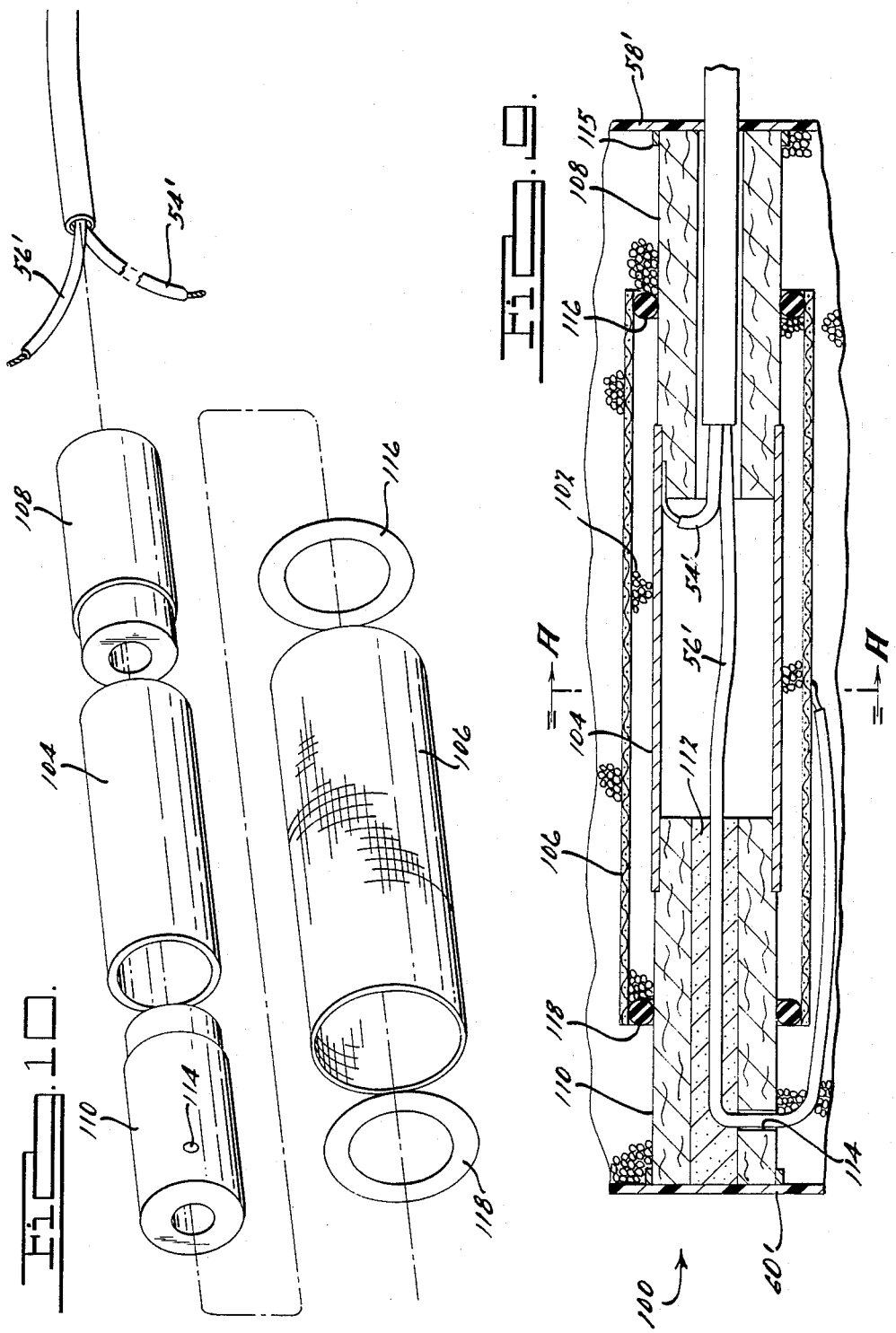

MOISTURE SENSING SYSTEM FOR AN IRRIGATION SYSTEM

CROSS REFERENCE TO RELATED APPLICATION

This application is a continuation-in-part application of U.S. Ser. No. 864,421, filed May 19, 1986, now Pat. No. 4,837,499.

BACKGROUND OF THE INVENTION

The present invention generally relates to automatic irrigation systems, and particularly to a moisture sensing device which will allow irrigation to occur only when the soil requires it.

Most automatic irrigation systems today use the same method of operation, namely time control. These irrigation systems employ a controller which acts as a multi-station timer which will turn the water sprinklers on and off at predetermined intervals These predetermined turn on and duration times will be programmed into the controller by the homeowner, landscaper or turf manager.

One of the drawbacks of these time based irrigation systems is that the controller must be reprogrammed regularly to keep from over or under-watering the area to be irrigated at different times of the year. In order to dispense water to the field being irrigated most efficiently, the ideal irrigation system would water only when soil conditions warranted. Specifically, only the amount of water required to replace the amount of moisture expended through evapotranspiration ("ET") should be dispensed by the irrigation system ET is the total amount of water which moves from the soil to the air in given amount of time due to evaporation directly from the soil and the transpiring from the grass itself. The ET level rises with increases in sunshine, wind and temperature, and decreases in relative humidity.

Present methods for replacing the moisture lost to ET include lengthy calculations based on data collected every day relating to micro-climate conditions. While this method works well for watering a large agricultural complex, the cost is impractical for most turf grass applications. Another technique for controlling the amount of irrigation in response to changing climate conditions is the use of a device to sense the amount of moisture present in the soil. A number of moisture sensors have been proposed, as will be briefly discussed below.

The most accurate type of moisture sensor is generally considered to be the neutron probe. Neutron probes are used by soil engineers to do soil moisture sampling on a weekly basis at large farms. These devices are relatively costly and they also require the use of radioactive materials in their operation.

One very old method of sampling soil moisture levels is to use a type of material which will expand and contract with varying degrees of moisture, such as wood or sponge. The expansion and contraction will usually raise or lower a diaphragm which controls water flow either directly or through electrodes making contact with each other. One of the drawbacks to this technique of sensing soil moisture is that a generally higher degree of accuracy is required for regulating an irrigation controller.

Another type of moisture sensor uses heat diffusion to determine if enough moisture is present in the soil to prevent watering. An example of such a moisture sensor is set forth in the U.S. Pat. No. 3,847,351, issued to Hasenbeck on November 12, 1974. Generally speaking, this type of moisture sensor employs a thermistor which is located in a number of glass beads which are in turn surrounded by a porous material which allows water to come and go When the system activates, the thermistor will heat up and the electronics for the sensor will measure the heat diffusion. If the soil is wet, and hence the beads are wet, then the heat will diffuse rapidly and the sensor electronics will prevent a solenoid from turning on and watering the field to be irrigated. If the beads are dry, then the heat will not diffuse as rapidly and the sensor electronics will permit the solenoid to be energized.

Another type of moisture sensor uses vacuum as a measure of the moisture in the soil. For example, tensiometers, which measure soil vacuum pressure in centibars, are the most widely accepted sensor for regulating the operation of a irrigation controller. The tensiometers are planted in wet soil and their gauges are initially set to zero. As the turf expends moisture through ET. additional moisture is drawn up from the soil through capillary action. This produces a vacuum which increases as the amount of moisture decreases. When the tensiometer gauge reaches a preset vacuum level, magnetic pick-ups complete a circuit which will allow the controller to begin irrigating the field.

Another type of moisture sensor is based on an electrical resistance which varies with the moisture level. Typically. in this type of sensor, two metal probes are separated by a couple of inches in a gypsum block. A regulated voltage is applied to one of the probes. and the voltage returning from the other probe is compared to it. The amount of current passing between the probes is dependent upon the level of moisture in the soil, because water conducts electricity. Besides gypsum blocks, other materials have been used as the porous sensor medium, including various granular materials and the soil itself. However, one of the drawbacks of this sensor design is that a wider range of resistance variation is needed to provide a good correlation to the exact amount of moisture in the soil.

Another form of moisture sensor is described in U.S Pat. No. 3,626,286, issued to Rauchwerger on December 7, 1971. This patent describes a sensor in which two plates or electrodes are separated and placed in the soil itself. The plates hold more electrons when the soil is dry because fewer of the electrons can leak to the other side due to the presence of conductive moisture in the soil between the plates. An electronic circuit is also described which measures the capacitance of the probes or plates. This capacitance value is used to determine if enough moisture exists in the soil to prevent the watering of the soil. One of the drawbacks to this type of moisture sensor is that the soil itself is used as the dielectric material of the capacitor. This causes a variation in the performance of the moisture sensor due to differing soil compositions.

Accordingly, it is a principal objective of the present invention to provide a moisture sensing device which will permit the efficient replacement of water lost to ET without requiring the collection of micro-climate data.

It is another objective of the present invention to provide a moisture sensing device which is capable of being retrofitted into existing automatic irrigation systems using standard time control operation.

It is another objective of the present invention to provide a moisture sensing device which requires little or no maintenance, and which may be easily adjusted.

It is a further objective of the present invention to provide a moisture sensing device whose accuracy is not dependent upon the composition of the soil being tested.

It is also an objective of the present invention to provide a moisture sensing device which is capable of automatically acting as a delay mechanism when the moisture level in the soil is close to being dry enough to allow for full cycle watering.

SUMMARY OF THE INVENTION

To achieve the foregoing objectives, the present invention provides a moisture sensing device which generally comprises a pair of concentrically disposed cylindrical conductors which are separated by a layer of bead-like material, such that a capacitor is formed whose resistance will vary in response to the level of moisture present in the fibrous material. An electrical circuit is connected across the cylindrical conductors for measuring the variable resistance caused by the level of moisture present in the layer of bead-like material. If the soil is dry enough to require watering, the sensor circuit will produce an output signal to the appropriate solenoid in the irrigation system to permit watering.

In the preferred form of the invention, the outer cylindrical conductor is constructed of an electrically conductive mesh material. while the inner cylindrical conductor is constructed of a solid electrically conductive material. The inner cylindrical conductor is shorter in length than the outer mesh conductor, and the inner cylinder is supported by a pair of opposing nonconductive members. In order to coaxially support the outer mesh conductor, an o-ring is interposed between the outer mesh conductor and each of the nonconductive members.

Additional advantages and features of the present invention will become apparent from a reading of the detailed description of the preferred embodiment which makes reference to the following set of drawings:

BRIEF DESCRIPTION OF THE DRAWINGS

FIG. 5 is a schematic diagram of a sensor circuit according to the present invention.

FIG. 6 is a perspective view of a moisture sensor according to the present invention.

FIG. 7 is an exploded assembly view of the moisture sensor shown in FIG. 6.

FIG. 8 is a cross-sectional view of the moisture sensor shown in FIGS. 6 and 7.

FIG. 9 is a longitudinal cross-sectional view of another embodiment of a moisture sensor according to the present invention.

FIG. 10 is a partial exploded assembly view of the moisture sensor shown in FIG. 9.

DETAILED DESCRIPTION OF THE PREFERRED EMBODIMENT

Figure 1:
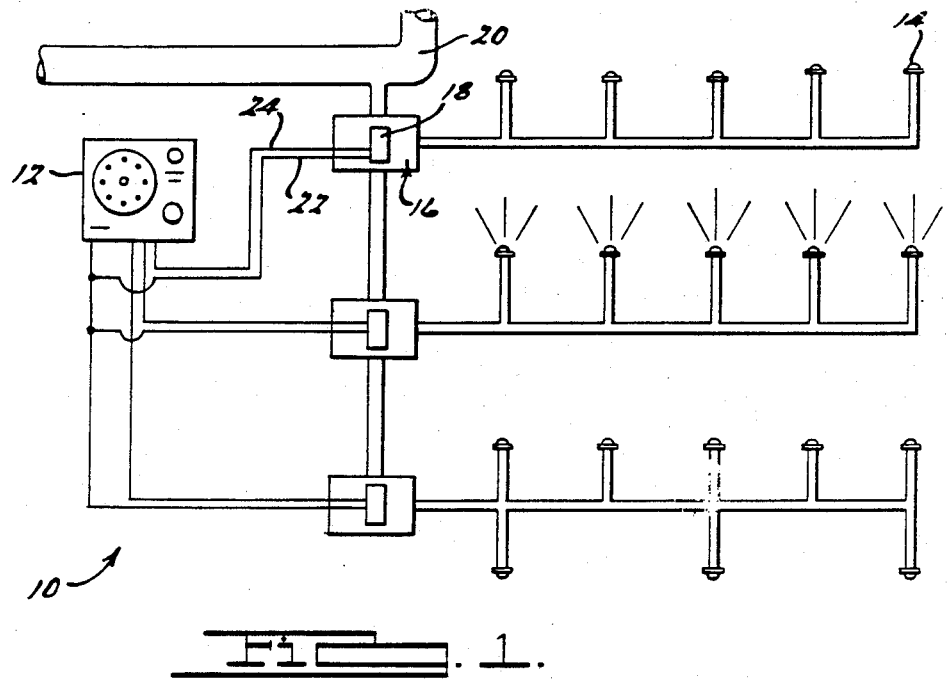
FIG. 1 is a schematic diagram of a conventional time-control based irrigation system.

Referring to FIG. 1, a schematic diagram of an irrigation system 10 is shown. The irrigation system 10 is a conventional irrigation system which is based upon a time control operation. The irrigation system 10 generally includes a central controller 12 and a plurality of sprinkler heads 14 which are arranged in groups referred to as stations. The irrigation system 10 also includes a plurality of solenoid valve operated station boxes 16 which are used to control the flow of water to the sprinkler heads 14. Each of the station boxes 16 includes a solenoid valve 18 which will permit water to flow from a main water pipe 20 to the sprinkler heads for that station in response to an appropriate output signal from the central controller 12. In general, most central controllers 12 today operate from a standard 112 volt AC supply. The output signal of such a central controller is typically a 24 volt AC output signal which is transmitted to the solenoid valves 18 via conductors 22 and 24 when it is desired to energize these solenoid valves.

The central controller 12 is a timer which is typically programmable on a three tiered basis. There are separate controls that determine which days of the week to irrigate, what times of the day to call for irrigation, and the time duration of the application at each station. For example, the central controller 12 may be programmed to cause each of the stations to water every other day once a day. Additionally, each of the stations may be programmed to have a different duration of irrigation. For example, one station might be programmed for a six minute application while another station may be programmed to provide a four minute application. Additionally, the central controller 12 is typically programmed to rotate through the stations so that only one of the solenoid valves 18 is energized at any one time. Thus, for example, as soon as the timing cycle for one station is completed, the power may be routed to another solenoid valve which will permit water to be distributed to the next group of sprinkler heads. When all of the stations have been watered, the central controller 12 will wait until the next programmed watering before starting the cycle over again. The number of stations which a central controller can operate typically varies from four to twenty-three stations, depending on the make and model of the controller.

Figure 2:
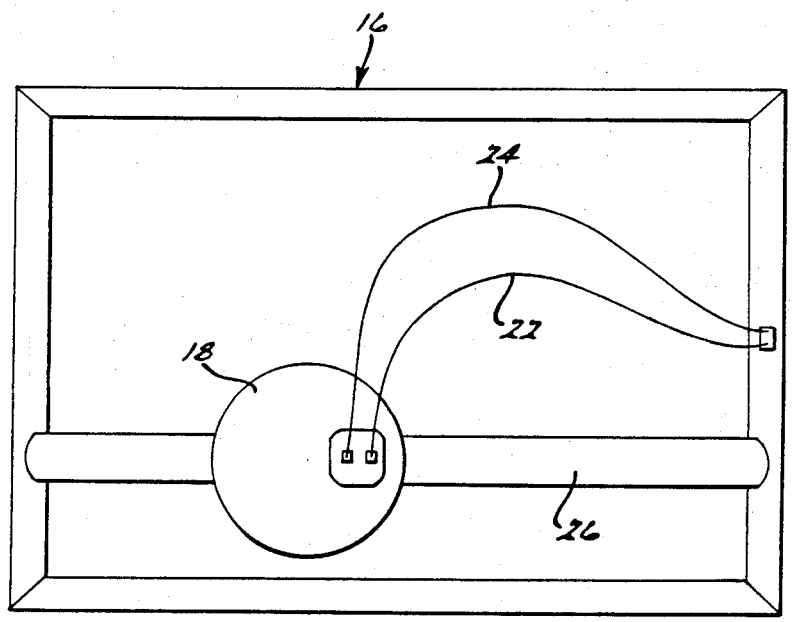
FIG. 2 is a schematic diagram of one of the solenoid valve operated stations shown in FIG. 1.

Referring to FIG. 2, a schematic diagram of one of the station boxes 16 is shown. Specifically, FIG. 2 illustrates that the solenoid valve 18 is connected to a water pipe or conduit 26 which leads to the group of sprinkler heads 14 which comprise its station for the irrigation system. The station box 16 is usually located near the group of sprinklers for that station in the irrigation system. Quite often, these station boxes 16 are made of green impact resistant plastic and are buried so that the lid of the box is flush with the ground.

One of the advantages of the present invention is that the moisture sensing device to be described herein can be easily retrofitted into an existing irrigation system, such as the irrigation system 10 described above. However, it should be appreciated that the principals of the present invention are not limited to any particular type of irrigation system, and that the irrigation system described above has been set forth for exemplary purposes only. Without the use of a cost efficient and accurate moisture sensing device, it will be appreciated that the irrigation system 10 will be over-watering the field covered by the sprinkler heads 14 most of the time, as the watering schedule will generally be set up to meet the highest ET rates for that time of the year. Aside from a substantial waste of water resources, it should also be appreciated that such over-watering may be also detrimental to the particular turf being irrigated.

Figure 3:
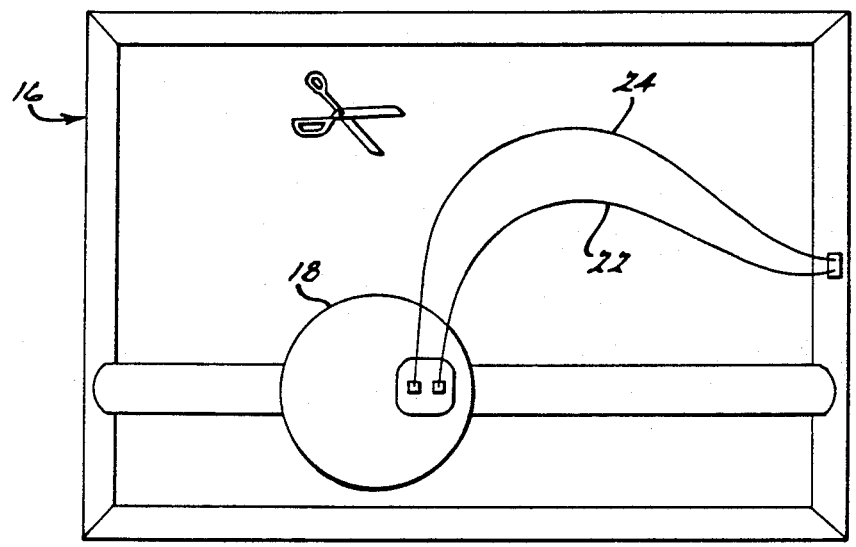
FIGS. 3 and 4 illustrate how a moisture sensing device according to the present invention may be retrofitted into the solenoid valve operated station shown in FIG. 2.
Figure 4:
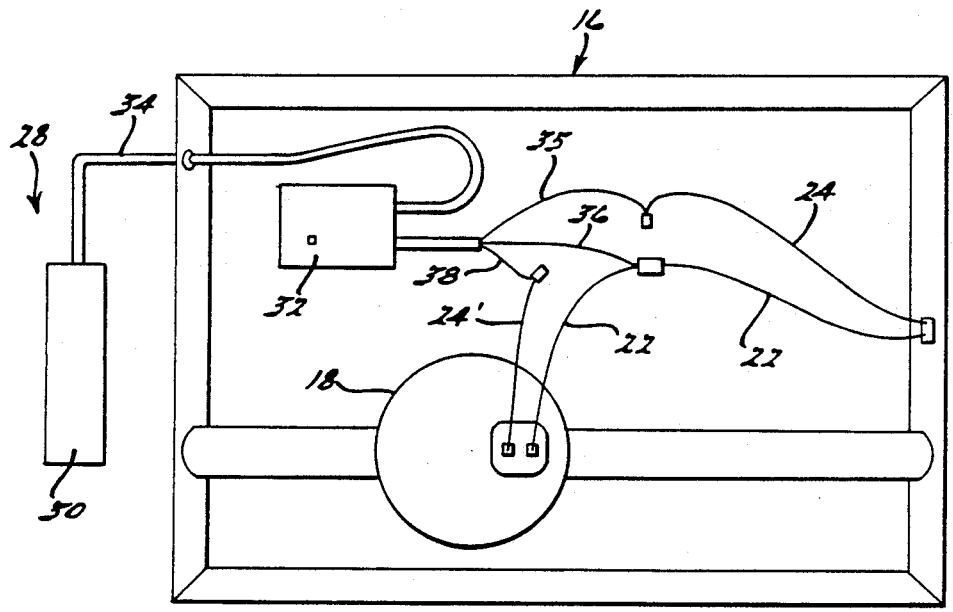

Referring to FIGS. 3 and 4, these figures show how the station box 16 may be modified so that a moisture sensing device 28 according to the present invention may be installed into an existing irrigation system. The moisture sensing device 28 will augment the irrigation system by providing a means to cut-off the electrical current flow to the solenoid valve 18 when the soil moisture levels are high enough to make watering inadvisable. The moisture sensing device 28 according to the present invention generally comprises a moisture sensor 30 and an electronic circuit 32. The moisture sensor 30 should be installed in the driest area within the station to be affected, and should be buried just below the root zone of the turf. The moisture sensor 30 is connected to the electronic sensor circuit 32 via electrical cable 34. The moisture sensing circuit 32 is preferably enclosed in a waterproof plastic container which is mounted in the station box 16. The moisture circuit 32 is connected to the irrigation system by simply cutting the "common" electrical conductor to the solenoid valve 18, such as "common" wire 24. Conductor 35 from the circuit 32 is attached to one of cut ends 24, while another conductor 38 from circuit 32 is attached to the other cut end 24'. In addition. third conductor 36 is spliced into conductor 22, as shown in FIG. 4 Specifically, the conductors 35 and 36 are used to provide electrical power to the moisture sensing circuit 32, while the conductor 38 is used an output to control the flow of electrical current to the solenoid valve 18.

Referring to FIG. 5, a schematic diagram of the moisture sensing circuit 32 is shown. The moisture sensing circuit 32 includes a rectification diode $D_1$, and a low pass filter which is comprised of resistor $R_1$ and capacitor $C_1$. The moisture sensing circuit 32 also includes a zener diode $Z_1$ which is used to protect the circuit from high voltage spikes.

The moisture sensing circuit 32 includes a pair of voltage dividers which provide the input signals to an operational amplifier comparator 40. The first voltage divider is comprised of resistors $R_2$ and $R_3$ which are connected across the power supply conductors 34 and 36. One of the inputs to the comparator 40 is connected to the junction between the resistors $R_2$ and $R_3$. The second voltage divider is comprised of the resistor $R_4$ and the moisture sensor 30. As will be appreciated from the description in FIG. 6, the moisture sensor 30 forms a capacitor whose resistance varies with the level of moisture being sensed. This second voltage divider is connected in parallel with the first voltage divider, and the remaining input to the comparator 40 is connected to the junction or node between resistor $R_4$ and the moisture sensor 30. It should also be noted that the resistor $R_3$ is preferably a potentiometer which will permit an adjustment of the turn on point of the comparator to be readily made.

When the moisture level sensed by the moisture sensor 30 is below the point where irrigation should be prevented. the comparator 40 will generate a high output when the moisture sensing circuit 32 receives power from the central controller 12 via conductors 35 and 36. This high output from the comparator 40 will cause the transistor $Q_1$ to conduct or turn on. The conduction of transistor $Q_1$ will cause the SCR $Q_2$ to be grated on at the appropriate point in the AC wave form. The conduction of the SCR $Q_2$ will cause a light emitting diode in the opto-isolator 42 to generate a sufficient amount of light that the triac in the opto-isolator will conduct. This will cause a gate turn on signal to be applied to the triac $Q_3$, which will in turn permit electrical current to flow to the solenoid valve 18. A listing of the specific part numbers and/or component values for the components in the moisture sensing circuit are set forth below in Table I.

TABLE I

| Reference Numeral | Part/Value |
| --- | --- |
| $R_1$ | 390 ohms |
| $R_2$ | 10 k |
| $R_3$ | 100 k |
| $R_4$ | 10 k |
| $R_5$ | 1 k |
| $R_6$ | 1 k |
| $R_7$ | 1 k |
| $R_8$ | 180 k |
| $R_9$ | 470 k |
| $R_{10}$ | 2.2 k |
| $C_1$ | 10 1f |
| $C_2$ | .2 1f |
| $C_3$ | 22 1f |
| $Q_1$ | 2N3906 |
| $Q_2$ | 2N5060 |
| $Q_3$ | 2N6071 |
| $Z_1$ | 1N970A |
| 40 | LM393 |
| 42 | MOC3009 |

While temperature effects on the moisture sensing device 28 are considered to be negligible, the circuit 32 could be modified to counteract changes in ground temperature, if desired. For example, a thermistor could be added which would provide a change in resistance opposite to the change induced in the sensor itself. Alternatively a second or reference sensor could be provided and sealed with a fixed amount of water inside. Since both sensors would change with temperature, but only one would change with the moisture level, the second sensor could provide a reference for comparison purposes.

Referring to FIGS. 6–8, three views of the moisture sensor 30 are shown. The moisture sensor 30 generally comprises a pair of concentrically disposed cylindrical conductors 44 and 46. The conductors 44 and 46 are separated by a layer of fibrous material 48 which acts as a dielectric to the capacitor which is formed by the combination of these three elements. The conductor 44 is preferably made out of an electrically conductive mesh material, such as stainless steel, and the conductor 46 is preferably made from a solid stainless steel tube. Similarly, the fibrous material 48 is preferably made out of a synthetic fibrous material, such as polyfoam, which has been wrapped around the cylinder or tube 46.

The moisture sensor 30 may also include an outer cylindrical shell 50 which is separated from the outer conductor 44 via an additional layer 52 of the fibrous material. Preferably, the outer cylindrical shell 50 is made out of an electrically nonconductive mesh material, such as plastic. It will be appreciated from the above that the moisture sensor 30 is constructed to permit easy ingress and egress of moisture through the sensor. The cylindrical conductors 44 and 46 may be connected to the moisture sensing circuit 32 by any conventional means, such as soldered wire connections 54 and 56. Additionally, the moisture sensor 30 may be provided with plastic end caps 58 and 60 at each end of the cylindrical outer shell 50 for protection and aesthetics.

In one form of the present invention, the shell 50 comprises a unitary plastic cage 62 which secures a fine plastic screen 64. Additionally, a pair of plastic end caps 66 and 68 may also be fitted over the ends of the cylinder 46. While the sensor 30 is shown to be in the form of a cylinder, it should also be appreciated that other suitable forms may be provided. For example, a flat design could be provided, in which the fibrous material could be interposed between two generally flat or square conductors. In such a case, both of the conductors should be made from an electrically conductive mesh material. so as to allow for moisture or water to pass easily through the sensor.

When electrical power is supplied to the two conductors 44 and 46, the capacitor formed by these conductors in combination with the fibrous material 48 will gradually charge up until a peak is reached. At this peak level, the amount of electrons sticking to the conductors 44 and 46 will equalize with the number of electrons leaking to the other side. During the charging of this "leaky" capacitor, the resistance of the moisture sensor 30 rises steadily until equilibrium is reached. This property acts as a delay mechanism if the soil moisture level is close to being dry sufficiently to allow for full cycle watering. Thus, the solenoid valve 18 might not be activated until several minutes after the central controller 12 has sent an energization signal to that station. This results in the duration of irrigation for that cycle being reduced by the delay time. Accordingly, a partial watering cycle will occur, which enables the moisture sensing device 28 to control the duration of the application of water at each station.

With respect to the installation of the moisture sensor 30, it is recommended that it be planted horizontally in the driest practical position for its station. The sensor 30 should be drenched in water, and the thumbwheel potentiometer $R_3$ should be rotated to the low or dry position. The station circuit 32 should be energized, and the thumbwheel should then be turned toward the wet position until the solenoid valve 18 clicks on. The irrigation system may then be switched to an auto control mode.

Additionally, it should be noted that the size of the sensor 30 may be varied in the appropriate application. However, the size of the sensor core and the gap between the conductors 44 and 46 may affect the response of the sensor. Accordingly, it is to be noted that in one form of the present invention, it is preferred that the outer diameter of the inner conductor 46 be approximately ⅜ inch and the inner diameter of the outer conductor 44 be approximately ⅞ inch.

Figure 11:
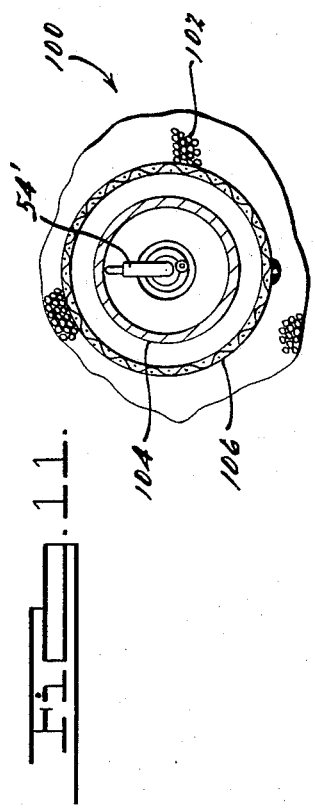
FIG. 11 is a cross-sectional view of the moisture sensor taken along lines A—A of FIG. 9.

Referring to FIGS. 9–11, three different views of a moisture sensor 100 is shown. The construction of the moisture sensor 100 is similar in some respects to that of the moisture sensor 30, such as the use of the same shell 50. Accordingly, corresponding structural components are indicated in FIGS. 9–11 by having their reference numerals primed. Thus, for example, the wire conductors 54' and 56' of the sensor 100 correspond to the wire conductors 54 and 56 of the sensor 30.

One of the principal differences between these two sensor constructions is that the sensor 100 uses glass beads 102 in the place of the layers 48 and 52 of the fibrous material used in the sensor 30. While it may be desirable to continue using the fibrous material as one of the layers and the glass beads as the other layer, it is preferred that the glass beads be used in substitution for both of the layers 48 and 52 of the sensor 30.

The average diameter of the glass beads 102 should be in the range of 200–800 microns, and the glass beads may in fact comprise a mixture of glass bead diameters in this range. While other bead-like materials may be employed (e.g., plastic or ceramic beads), glass beads are preferred due to their low cost and availability. In this regard, it should be appreciated that the beads are used to simulate the surrounding soil, and that the size of the beads will determine, at least in part, how long the moisture will be retained in the sensor. It should also be appreciated that the range of glass bead diameters selected should be such as to be easily contained within the plastic screen 64' of the cylindrical outer shell 50'.

Figure 12:
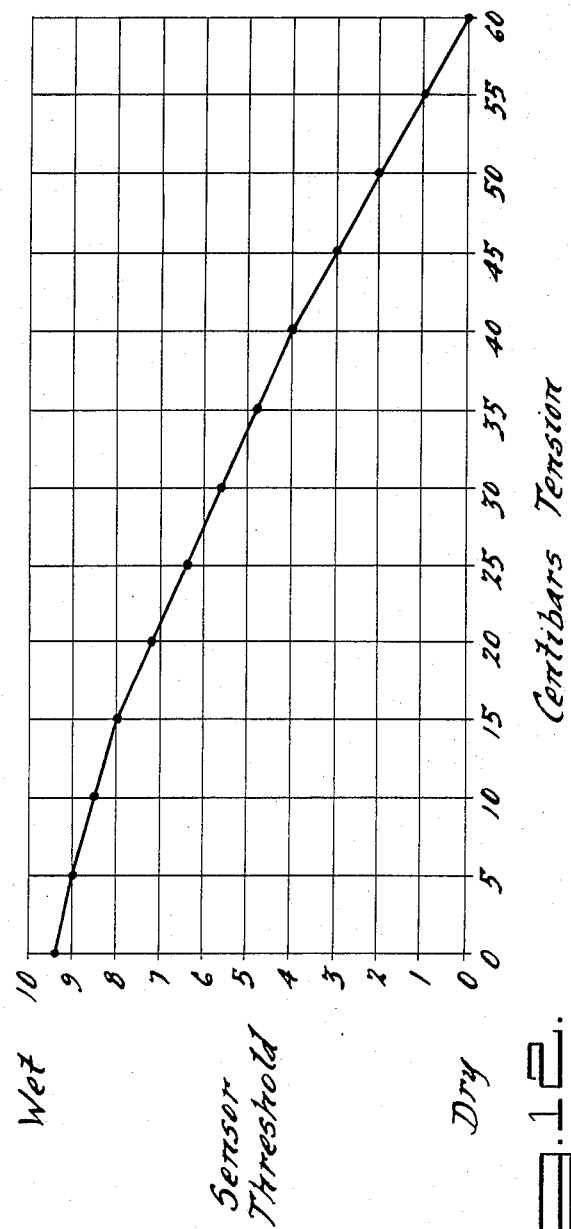
FIG. 12 is a graph illustrating an average response curve for the moisture sensor shown in FIGS. 9—11.

With respect to the embodiment described, it is preferred that the average diameter of the beads 102 be in the range of 200–250 microns. This preferred size is selected relative to the particular electrode configuration of the sensor 100 to provide a desired conductivity for the sensor. In the sensor 100, the inner cylindrical electrode 104 is shorter than the outer cylindrical electrode 106, and the 200–250 micron bead size helps to compensate for this difference in the conductive area of the electrodes. The result of this concentric electrode configuration and bead size combination enables a nearly linear response to be achieved by the sensor 100. In this regard. FIG. 12 is a graph which shows an average response curve for the sensor 100 using a 200 micron average bead size.

Referring again to FIGS. 9–11, the inner conductor 104 is shown to be constructed of a solid electrically conductive material, while the outer conductor 106 is shown to be constructed of an electrically conductive mesh material. The inner conductor 104 is supported between a pair of rigid members 108–110. The rigid members 108–110 are preferably constructed of plastic, but may be made from any suitable material which is electrically nonconductive. The rigid members 108–110 may be mounted to the inner conductor 104 by any suitable means, such as a press fit relationship. While the rigid member 108 is hollow to permit the sheathed wires 54' and 56' access to the interior of the sensor, the central bore in the rigid member 108 may be filled with a suitable cement epoxy 112 after the wire 56' is drawn through the aperture 114 in the side of the member. In this regard, it should be appreciated that the aperture 114 is provided in order to permit the wire 56' to be connected to the outer conductor 106. While other suitable connecting arrangements may be made, this particular construction enables the nonconductive members 108–110 to extend all the way to engage their respective end caps 58' and 60'. The end caps 58' and 60' may be provided with tabs 115 to help support the rigid members 108–110. However, it should be noted that the packing of glass beads 102 throughout the sensors will also serve to hold the electrode assembly in place.

The outer conductor 106 is coaxially supported over the inner conductor 104 by a pair of elastomeric o-rings 116–118. Specifically. each of the o-rings 116–118 are interposed between the outer conductor 106 and one of the rigid members 108–110. As shown in FIG. 9, the inner conductor is centrally or concentrically disposed within the outer conductor 106, such that a spaced is provided between the ends of the inner conductor and the ends of the outer conductor. This difference in length between the conductors or electrodes 104-106 serves to avoid a miniscus from forming around the area of the o-rings 116-118. While the inner conductor 104 is about sixty percent as long as the outer conductor 106, other suitable variations in length may be employed in the appropriate application.

It will be appreciated that the above disclosed embodiment is well calculated to achieve the aforementioned objectives of the present invention. In addition, it is evident that those skilled in the art, once given the benefit of the foregoing disclosure, may now make modifications of the specific embodiment described herein without departing from the spirit of the present invention. Such modifications are to be considered within the scope of the present invention which is limited solely by the scope and spirit of the appended claims.

I claim:

1. A moisture sensing device, comprising:
 a sensor having a pair of concentrically disposed conductors, each said conductor being in the form of a hollow cylinder, and both said conductors being contained in a generally cylindrical enclosure having screen means for permitting moisture to ingress and egress through said sensor, said conductors being separated by a porous layer of dielectric bead-like material to form a capacitor whose resistance will vary in response to the level of moisture present in said dielectric bead material, a porous layer of said bead-like material also being interposed between the outer one of said conductors and said enclosure, said outer conductor being constructed of an electrically conductive, tubular formed mesh material and having a different length than the inner one of said conductors; and
 circuit means connected across said conductors for measuring the variable resistance caused by the level of moisture present in said dielectric bead material.

2. The moisture sensing device according to claim 1, wherein said circuit means includes a comparator having one input connected to the junction between first and second resistors and a second input connected to the junction between a third resistor and said capacitor.

3. The moisture sensing device according to claim 2, wherein said first and second resistors form a first voltage divider across a power supply, and said third resistor and said capacitor form a second voltage divider across said power supply.

4. The moisture sensing device according to claim 2, wherein one of said first and second resistors is a potentiometer for adjusting the threshold level of said comparator.

5. The moisture sensing device according to claim 4, wherein the output of said comparator controls the gating of an electronic switching circuit having optical means for isolating the gating signal of said circuit means.

6. The moisture sensing device according to claim 1, wherein said dielectric bead-like material is comprised of glass beads having an average diameter substantially equal to or greater than 200 micron.

7. The moisture sensing device according to claim 1, wherein the inner one of said conductors is constructed of an electrically conductive solid material.

8. The moisture sensing device according to claim 5, wherein said inner conductor is shorter than said outer conductor.

9. The moisture sensing device according to claim 8, wherein said inner conductor is supported by a pair of opposing nonconductive members.

10. The moisture sensing device according to claim 9, wherein said outer conductor is supported by a pair of o-rings which are interposed between said outer conductor and said nonconductive members.

11. A moisture sensing device, comprising:
 an enclosure which is generally cylindrical in shape and constructed of a nonconductive material, said enclosure including a unitary cage which secures screen means for permitting moisture to pass through said enclosure, and a pair of end caps secured to said cage;
 a first conductor which is generally cylindrical in shape and constructed of an electrically conductive solid, yet hollow material, said first conductor being supported between a pair of nonconductive members, one of said nonconductive members being hollow to permit a wire to pass through said nonconductive member;
 a second conductor having a tubular cylindrical shape and constructed of an electrically conductive mesh material, said first conductor being coaxially disposed within said cage of said enclosure, said second conductor being substantially longer than said first conductor;
 a first porous layer of dielectric bead material interposed between said first and second conductors, and a second porous layer of said dielectric bead material interposed between said second conductor and said cage of said enclosure; and
 said first and second conductors and said first porous layer forming a capacitor whose resistance will vary in response to the level of moisture present in said dielectric bead material;
 circuit means connected across said first and second conductors for measuring the variable resistance caused by the level of moisture present in said dielectric bead material.

12. The moisture sensing device according to claim 11, wherein said dielectric bead material is comprised of glass beads having an average diameter substantially equal to or greater than 200 microns and no larger than approximately 800 microns.

13. The moisture sensing device according to claim 11, wherein said second conductor is supported by a pair of o-rings which are interposed between said second conductor and said nonconductive members.

* * * * *

UNITED STATES PATENT AND TRADEMARK OFFICE
CERTIFICATE OF CORRECTION

PATENT NO. : 4,952,868

DATED : August 28, 1990

INVENTOR(S) : Robert P. Scherer, III

It is certified that error appears in the above-identified patent and that said Letters Patent is hereby corrected as shown below:

Title Page, line 1 of Abstract after "system" insert --is disclosed--

Column 1, line 20, after "intervals" insert --.--

Column 1, line 33, after "system" insert --.--

Column 1, line 35, after "air in" insert --a--

Column 2, line 6, after "go" insert --.--

Column 2, line 22, after "ET." should be --ET,--

Column 2, line 31, "Typically." should be --Typically,--

Column 2, line 33, "probes." should be --probes,--

Column 2, line 44, after "S" insert --.--

Column 3, line 30, "material." should be --material,--

Column 5, line 34, after "Figure 4" insert a --.--

Column 5, line 37, before "an" insert --as--

Column 5, line 67, "prevented." should be --prevented,--

UNITED STATES PATENT AND TRADEMARK OFFICE
CERTIFICATE OF CORRECTION

PATENT NO. : 4,952,868

DATED : August 28, 1990

INVENTOR(S) : Robert P. Scherer, III

It is certified that error appears in the above-identified patent and that said Letters Patent is hereby corrected as shown below:

Column 6, line 4, "grated" should be --gated--

Column 7, line 18, "material." should be --material,--

Column 8, line 32, "regard." should be --regard,--

Column 8, line 64, "Specifically." should be --Specifically,--

Column 10, line 4, Claim 6, "micron" should be --microns--

Column 10, line 8, Claim 8, "5" should be --7--

Signed and Sealed this

Twenty-first Day of January, 1992

*Attest:*

HARRY F. MANBECK, JR.

*Attesting Officer*  *Commissioner of Patents and Trademarks*